United States Patent [19]

Giaever et al.

[11] Patent Number: 4,619,904

[45] Date of Patent: Oct. 28, 1986

[54] AGGLUTINATING IMMUNOASSAY USING PROTEIN-COATED LIQUID DROPLETS

[75] Inventors: Ivar Giaever, Schenectady; Charles R. Keese, Schoharie, both of N.Y.

[73] Assignees: General Electric Company, Schenectady, N.Y.; National Foundation for Cancer Research, Inc., Bethesda, Md.

[21] Appl. No.: 665,867

[22] Filed: Oct. 29, 1984

[51] Int. Cl.[4] ............... G01N 33/543; G01N 33/544; A61J 5/00; B32B 5/16

[52] U.S. Cl. .................................... 436/518; 264/4.1; 428/402.2; 436/528; 436/800; 436/804; 436/829

[58] Field of Search .................. 428/402.2; 436/528, 436/829, 800, 804, 518; 264/4.1

[56] References Cited

U.S. PATENT DOCUMENTS

| | | | |
|---|---|---|---|
| 3,406,119 | 3/1965 | Kosar et al. ........................ 264/4.1 |
| 3,779,942 | 12/1973 | Bolles ............................... 428/402.2 |
| 3,970,518 | 7/1976 | Giaever ............................. 424/12 |
| 4,018,886 | 4/1977 | Giaever et al. ................... 424/12 |
| 4,041,146 | 8/1977 | Giaever ............................. 424/12 |
| 4,308,165 | 12/1981 | Vassiliades et al. ............. 264/4.1 |

FOREIGN PATENT DOCUMENTS

| 0087036 | 5/1984 | Japan .............................. 264/4.1 |
|---|---|---|
| 2066203 | 7/1981 | United Kingdom ............. 436/528 |

Primary Examiner—Christine M. Nucker
Assistant Examiner—Stephen C. Wieder
Attorney, Agent, or Firm—William A. Teoli; James C. Davis, Jr.; James Magee, Jr.

[57] ABSTRACT

Small liquid droplets, coated with protein, the protein coating containing molecules of protein that will interact specifically with a select protein, are contacted with a liquid sample to determine the presence or absence of the select protein therein depending upon whether the droplets agglutinate.

21 Claims, 2 Drawing Figures

AGGLUTINATING IMMUNOASSAY USING PROTEIN-COATED LIQUID DROPLETS

BACKGROUND OF THE INVENTION

This invention relates to the detection of proteins by the utilization of the phenomenon by which such proteins interact specifically either immunologically or non-immunologically.

The preparation and use of protein-coated droplets dispersed in a tissue culture medium for growing cells is described and claimed in the U.S. patent application Ser. No. 443,311—Giaever and Keese, filed Nov. 23, 1982. This application is incorporated by reference.

The use of small magnetic particles coated with a protein that will interact specifically with a select protein in order to separate such select protein from a solution is disclosed in U.S. Pat. No. 4,018,886—Giaever. Also, the use of small magnetic particles coated with an antibody layer for sorting out and separating select viruses, bacteria and other cells from multi-cell, bacteria or virus populations is disclosed in U.S. Pat. No. 3,970,518—Giaever.

The use of inert molecules as "spacers" for molecules of interest is described in pending U.S. patent application Ser. No. 358,219—Giaever, filed Mar. 15, 1982 and assigned to the assignee of the instant application.

A common test for pregnancy involves coating small polystyrene latex spheres with the hormone, human chorionic gonadotropin (HCG). When a woman becomes pregnant, the level of HCG in the urine increases significantly. This is an indirect test in which a quantity (as determined by titer by an established procedure) of antibodies to HCG is added to a sample of female urine and is allowed to incubate for from about 5 to about 10 minutes therein. Next, HCG-covered latex spheres are mixed with the urine and the mix is allowed to incubate for from about 5 to about 10 minutes. If agglutination of the spheres takes place, the urine does not contain HCG to the level establishing a pregnant condition; if the spheres remain in single suspension, HCG was present beyond that level.

These tests can be generalized to detect any antigen or antibody. The fact of agglutination preferably should be visible to the ordinary observer.

U.S. patent application Ser. No. (665,902)—Giaever and Keese, filed, Oct. 29, 1984, discloses and claims an invention in which an emulsion (in which an aqueous medium contains small dispersed liquid droplets coated with a protein that will interact specifically with a select protein) is mixed with a liquid sample, time is allowed for interaction to occur and then the mixture is exposed to a tagged antibody specific to the select protein. After an appropriate hold time the emulsion is broken and the protein that previously covered the disperse droplets becomes concentrated at the interface between the two continuous phases. The interface is checked for the presence of the tagged antibodies to establish the presence or absence of the select protein. This application is assigned to the assignee of this invention and is incorporated by reference.

DESCRIPTION OF THE INVENTION

An emulsion is, typically, a heterogeneous system with at least one immiscible liquid dispersed in another in the form of droplets. The phase providing the droplets is the dispersed, or internal, phase while the phase providing the matrix for the dispersed phase is the continuous, or external phase.

According to this invention, a large number of small droplets of a first liquid are dispersed in a second liquid in the nature of an emulsion. The second liquid is an aqueous medium and the first liquid (specific gravity greater than one) is relatively immiscible with the second liquid. The resulting liquid droplets receive a coating comprising a specific protein (e.g., a coating of a particular antibody) that will biologically interact specifically with some select protein (e.g. a select antigen).

The initial protein coating can be provided in the aqueous medium used to prepared the emulsion or can be added after the emulsion has been prepared. Preferably the concentration of protein employed is known. A contact period between the protein material and the liquid droplets of less than one hour is usually sufficient, when protein concentrations upwards of 10 micrograms/ml. are employed.

In those instances in which the desired protein coating does not adhere to the liquid droplets unaided, the necessary attachment should be obtained chemically by introducing a small amount of a fluorinated polar compound (e.g., pentafluorobenzoyl chloride) to the first (i.e., the droplet) liquid.

Having coated the liquid droplets with the requisite specific protein, the emulsion is then gently centrifuged to segregate the droplets from the bulk of the aqueous medium. The supernatant aqueous medium is then removed (e.g., by decanting). Next, the coated droplets are washed at least once with an aqueous solution of a non-specific protein (about 100 micrograms of the non-specific protein per milliliter of 0.15 molar sodium chloride solution). The protein-coated droplets are then re-suspended in dilute (i.e., about 0.15 molar NaCl) saline solution at pH 7.5. It may be necessary to use a buffer, such as 0.01 molar tris(hydroxymethyl)aminomethane. These protein-coated liquid droplets present in a concentration of from about $10^6$ to about $10^{10}$ droplets/cc are now suitable for contact with a liquid sample to be tested for the presence or absence of the specific protein. The liquid sample is normally a body fluid, such as blood or urine.

Utilization of the protein-coated liquid droplets may be effectuated either by adding the sample of body fluid to the liquid volume containing the protein-coated liquid droplets or, vice versa. Once either addition has been made, the volume of liquid is subjected to a gentle rocking action for about 15 minutes to increase the number of contacts between the protein-coated droplets and the body fluid content. The volume is then inspected for the presence of agglutination, which would indicate that the specific biological reaction has occurred. Agglutination, of course, can occur only if the select protein has at least two binding sites.

The procedure can be modified to increase the sensitivity of the test by making the agglutination more effective. This can be accomplished by coating the liquid droplets with a mixture of proteins (one of which is the initial, or specific, protein and the rest of the protein content is non-specific to the select protein) such that the number of protein molecules available on the droplets to interact specifically with the select protein is a very small percentage of the mixture. With this arrangement, whereas approximately $10^4$ molecules will locate themselves over the surface of a 1 micrometer diameter liquid sphere, when utilizing the protein mixture, on the order of a few hundred of the specific protein molecules will distribute themselves at locations over the sphere by and large separated from each other by large numbers of the non-specific protein molecules. In this way, the interaction of the select protein molecules, if present, will, at least statistically, occur such that each select protein molecule will initially interact with one single specific protein molecule leaving one interactive site available for interconnection with an accommodating binding site on another liquid droplet thereby increasing the driving force for agglutination.

This modified procedure is of particular use, when the concentration of select protein in the sample is very high or quite low. Also, the ability to use smaller amounts of the specific protein becomes important when the specific protein is expensive.

Both fluorocarbon and silicone oils have been found suitable as liquid droplets in the practice of this invention. The fluorocarbons are characterized by lack of toxicity, inertness, high density (about 1.5 to 1.9 gm/cm$^3$), immiscibility with water, low solubility for most other materials, thermal and chemical stability, low viscosity, transparency and hydrophobicity. The fluorocarbon oils that have been used are the FC-43, FC-75, FC-104 oils marketed by the 3M Company, St. Paul, Minn. and alumina-treated FC-43 oils. In addition, work was done with silicone oil (General Electric Co. SF 1265).

Droplets having an average particle diameter of about 0.1 micrometers to 5.0 micrometers may be used in the practice of this invention. The typical average droplet diameter used was about one micrometer.

As a variant of the aforementioned embodiments the select protein molecules and/or the non-specific protein molecules employed to coat the droplets may be supplied with fluorescent or radioactive tag moieties to enhance detection of agglomeration.

The preparation of tagged biological particles is described in U.S. Pat. No. 4,041,146—Giaever.

Fluorescent tagging is the preferred mode of tagging. The procedure for fluorescent tagging as well as radioactive tagging are generally understood by those skilled in the art. Suitable methods for fluorescent tagging of an anchored layer of biological particles are thoroughly described in the aforementioned Handbook of Experimental Immunology in Chapter 18 "Immunofluorescence" by G. D. Johnson and E. J. Holborow.

Suitable methods for the radioactive tagging of biological particles are described in Principles of Competitive Protein-Binding Assays [Ed. W. D. Odell & W. H. Daughaday, Philadelphia: Lippincott (1971)] in Chapter X "Radioiodination of Peptide Hormones: Procedure and Problems" by F. C. Greenwood pp. 288–296. Another reference work which describes suitable radioactive tagging methods is in Radioimmunoassay Methods [Ed. K. E. Kirkham & W. M. Hunter, Churchill: Livingstone (1971)] "The Preparation and Assessment of Iodinated Antigens" by W. M. Hunter pp. 3–23 and "The Immuradiometric Assay" by G. M. Addison and C. N. Hales pp. 447–461.

These teachings are incorporated by reference as they are representative of the methods useful for tagging biological particles employed in the practice of the invention disclosed herein.

There are several advantages to using liquid droplets in place of solid spheres. First, liquid particles can deform and allow for a greater area of contact between adjacent particles in an agglutinated mass. The availability of this property means that the liquid shear forces that can be withstood by the agglutinated mass is high. Second, the oil emulsion is substantially uncharged and appears to be usable over a wide range of pH values compared to latex particles which must be used at pH 8. Third, experience with the emulsion to date has shown that it works very well in whole serum, while latex particles do not. Fourth, the density of the liquid droplets can be adjusted within wide limits.

BRIEF DESCRIPTION OF THE DRAWING

The subject matter of the instant invention for which protection is sought is presented as claims at the conclusion of the written description of the invention set forth herein. The description sets forth the manner and process of making and using the invention including the best mode contemplated therefor, and the accompanying drawing forms part of the description in that they schematically illustrate the practice of the invention.

The view shown in FIG. 1 shows apparatus for contacting the emulsion containing the cleansed specific protein-coated droplets according to this invention mixed with a sample liquid suspected of containing the select protein.

MANNER AND PROCESS OF MAKING AND USING THE INVENTION

Figure 1:
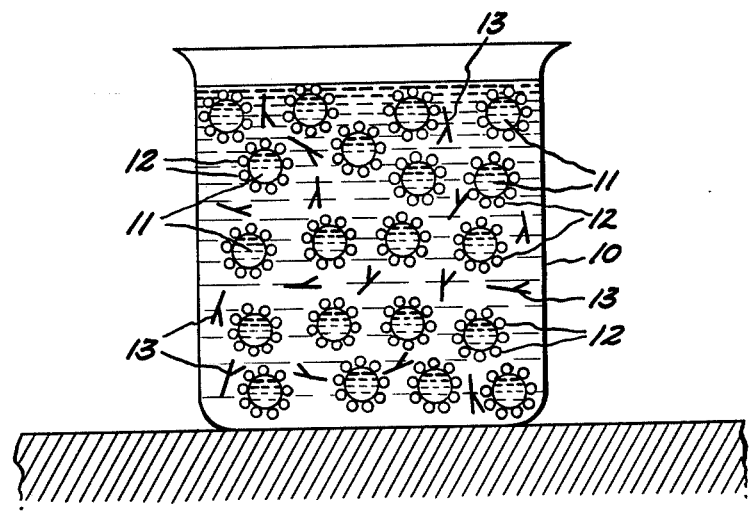

The apparatus and materials disclosed herein are merely exemplary and, after an understanding of the method of this invention, other embodiments may be readily devised.

Having identified the particular select protein (e.g., antibody or antigen) to be detected, a small amount of fluorocarbon oil is placed in a container (e.g. a beaker or test tube) together with a much larger quantity of an aqueous phase. Preferably the protein with which the liquid droplets are to be coated is introduced prior to emulsification. In such a case, typically about 20 milligrams of the specific protein in 3.5 ml. of saline (0.15 M NaCl; no buffer) is added to 100 microliters of the disperse phase (the oil). This would be the equivalent of about 1 to about 5 micrograms of protein per square centimeter of droplet surface area.

This liquid system is subjected to agitation (e.g., mechanical stirring, sonication) sufficient to bring about emulsification. A useful device for accomplishing this effect is the Polytron ® (Brinkman Instruments, Westbury, N.Y.), which simultaneously provides the actions of sonication and mechanical agitation. Operation of this device at a setting of 7 will yield droplets of the oil in the useful range of about 0.1 to about 5.0 micrometers in diameter. Depending upon the nature of the specific protein, an agitation period of about 1 to 4 minutes with this device will yield droplets having an average diameter of about 1 micrometer.

If the specific protein addition is made after the emulsification, the coating process may be less effective (i.e., agglutination may occur). Thus, for example, it has been found that droplet coating after emulsification with bovine serum albumin was successful, while the same sequence using IgG immunoglobulin was not successful.

Whether pre-emulsification or post-emulsification addition of the specific protein is employed, the protein should be added in excess of the amount theoretically required to coat the droplets in order to insure very rapid coating of the droplets.

As noted hereinabove, if the protein was not added prior to the emulsifying step, it would be added at this point and mixed with the emulsion by gentle agitation. After a sufficiently long contact period, the emulsion is cleansed to remove the excess specific protein.

Cleansing of the protein-coated droplets is accomplished by concentrating the protein-coated droplets as by gentle centrifugation, decanting the supernatant and then washing with a solution of non-specific protein. The concentrating, decanting and washing may be repeated as needed. After the washing step, the clean select proteincoated droplets are re-suspended in 0.15 molar NaCl with a buffer, if needed to provide a suitable pH. Care is to be taken, of course, in the cleansing operation not to break the emulsion.

The washing with non-specific protein is also important in that it helps to keep the protein-coated droplets stable.

Next, a volume of the liquid sample of body fluid to be assayed for specific protein content is brought into contact with (i.e., is added to and mixed with) the emulsion in which the protein-coated liquid droplets form the disperse phase. The period of mixing may vary from less than 5 minutes to as much as 30 minutes (depending upon concentration).

At this point, the distribution of the material content of beaker 10 schematically illustrated in FIG. 1 will prevail assuming that the liquid sample contains molecules of the select protein but insufficient time has elapsed for the specific interaction to occur. As shown, liquid droplets 11 are provided with a monomolecular coating of specific protein (e.g., an antigen) 12 which will interact specifically with the select protein for which the assay is being run. Molecules of the select protein (e.g., an antibody) distributed in the aqueous system are identified by numerals 13.

Figure 2:
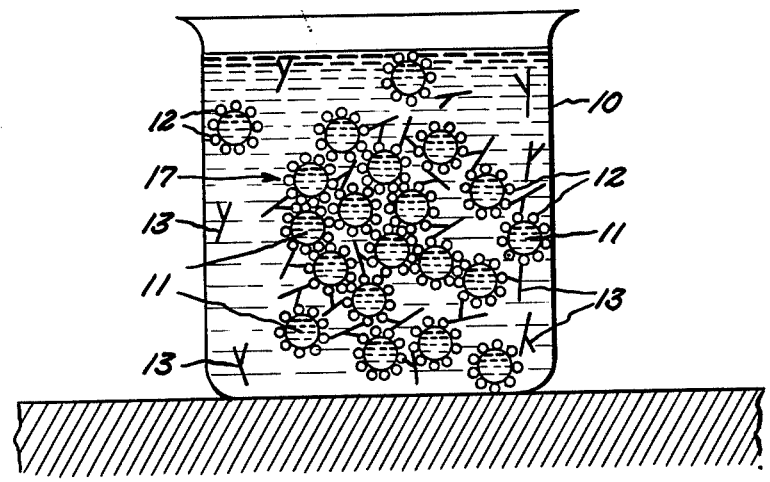
FIG. 2 shows the development of an agglutinated mass of the protein-coated liquid droplets in the system in FIG. 1.

The schematic representation of the agglomerated mass 17 in FIG. 2 is representative of results obtained in the practice of this invention when the appropriate amount of select protein molecules is present.

EXAMPLES

A series of tests were conducted on an emulsion prepared by operating a Polytron device at a setting of 7 for 4 minutes in a combination of 0.1 ml. of fluorocarbon oil (FC-43), 300 microliters of 10% by wt. bovine serum albumin and 3.5 ml. 0.15 M NaCl, which emulsion was washed with non-specific protein solution as described hereinabove. Thereafter, separate quantities of the clean emulsion were mixed with various concentrations of antibody to the bovine serum albumin in the form of antiserum (i.e., serum from an inoculated animal, such as a rabbit or a goat). The dilutions (antiserum to total volume) ranged from 1:10 to greater than 1:6400. A control (i.e., no antiserum) was also run. All dilutions from 1:10 to 1:6400 produced visible agglomeration. Dilutions of greater than 1:6400 and the control produced no visible agglomeration. The greatest degree of agglomeration occurred at antiserum concentrations of about 1:200.

In addition to the use of the bovine serum albumin and the rabbit antiserum thereto, similar results were obtained with rabbit IgG and the goat antiserum thereto and human serum albumin and the goat antiserum thereto.

These results with model systems are clearly illustrative of the practice of this invention and they also illustrate the broad range over which agglomeration will be evidenced.

If agglomeration is not evident, the process can be repeated to increase the effectiveness of agglomeration. In this modified process, initial coating of the droplets 11 with protein is accomplished by using a mixture of specific protein and non-specific protein in a ratio in the range of from about 1:30 to about 1:1000. Examples of such mixed proteins that have been successfully employed are bovine serum albumin (specific protein) together with human serum albumin (non-specific protein) and rabbit IgG (specific protein) together with goat IgG (non-specific protein). The optimum ratio of specific:non-specific protein in the mixture can be routinely determined.

This modified process is useful whether the lack of visible agglomeration is due to the presence of too many select protein molecules or due to too few of these molecules.

The detection of agglomeration can be augmented by using detectable tagged moieties affixed to the molecules of the specific protein when this is the only protein used initially to coat the droplets or to the molecules of non-specific protein (as well as to the specific protein, if desired), when a protein mixture is used to coat the droplets. Preferably fluorescent tags are employed, these being detected by exposure to ultraviolet light. Alternatively, radioactive tags can be used, these being detected by the use of a radiation counter. Detection of a strong signal of tag presence in some portion of the liquid system will be indicative of localized agglomeration.

What is claimed is:

1. The diagnostic method for determining the presence or absence of select protein in a liquid sample comprising the steps of:

(a) preparing an emulsion in which a first liquid is dispersed as a large number of small protein-coated liquid droplets in a second liquid, said second liquid being an aqueous medium, said first liquid being relatively immiscible with said second liquid, and the protein coating said droplets including molecules of a protein having the property of interacting specifically with said select protein;

(b) contacting the protein-coated droplets in said emulsion with a solution containing proteinaceous material and (c) determining the presence or absence of agglutination of the protein-coated droplets.

2. The method of claim 1 wherein the proteinaceous material is contained in serum.

3. The method of claim 1 wherein the diameters of the droplets are in the range of from about 0.1 micrometers to about 5 micrometers.

4. The method of claim 1 wherein the droplet density is in the range of from about $10^6$ to about $10^{10}$ droplets per cubic centimeter of emulsion.

5. The method of claim 1 wherein the second liquid is a fluorocarbon.

6. The method of claim 1 wherein the second liquid is silicone oil.

7. The method of claim 1 wherein the protein coating the droplets comprises antibody molecules.

8. The method of claim 1 wherein the protein coating the droplets comprises antigen molecules.

9. The method of claim 1 wherein protein molecules comprising the protein coating on said droplets have detectable tag moieties affixed thereto.

10. The method of claim 9 wherein the tag moieties are fluorescent tags.

11. The method of claim 9 wherein the tag moieties are radioactive tags.

12. A diagnostic device for determining the presence or absence of a select protein in a liquid sample comprising in combination a container, a plurality of small protein-coated liquid droplets dispersed in an aqueous medium in said container, the protein coating said droplets including molecules of a protein having the property of interacting specifically with said select protein.

13. The diagnostic device of claim 12 wherein the protein coating comprises antibody molecules.

14. The diagnostic device of claim 12 wherein the protein coating comprises antigen molecules.

15. The diagnostic device of claim 12 wherein the average diameter of the droplets is about 1 micrometer.

16. The diagnostic device of claim 12 wherein the droplet density is in the range of from about $10^6$ to about $10^{10}$ droplets per cubic centimeter of aqueous medium.

17. The diagnostic device of claim 12 wherein protein molecules comprising the protein coating on said droplets have detectable tag moieties affixed thereto.

18. The diagnostic device of claim 17 wherein the tag moieties are fluorescent tags.

19. The diagnostic device of claim 17 wherein the tag moieties are radioactive tags.

20. The diagnostic device of claim 12 wherein the protein coating consists of a mixture of molecules of protein able to interact specifically and molecules of non-specific protein.

21. The diagnostic device of claim 20 wherein the ratio of the molecules of protein able to interact specifically to the molecules of non-specific protein is in the range of from about 1:30 to about 1:1000.

* * * * *